United States Patent [19]

Bader et al.

[11] Patent Number: 5,430,188
[45] Date of Patent: Jul. 4, 1995

[54] PROCESS FOR THE PREPARATION OF 2-ALKYL-6-METHYL-N-(1'-METHOXY-2'-PROPYL)-ANILINE AND A PROCESS FOR THE PREPARATION OF THEIR CHLORACETANILIDES

[75] Inventors: Rolf Bader, Riehen; Peter Flatt, Binningen; Paul Radimerski, Therwil, all of Switzerland

[73] Assignee: Ciba-Geigy Corporation, Ardsley, N.Y.

[21] Appl. No.: 168,034

[22] Filed: Dec. 15, 1993

Related U.S. Application Data

[63] Continuation-in-part of Ser. No. 998,030, Dec. 12, 1992, abandoned.

[51] Int. Cl.6 ............................................. C07C 231/08
[52] U.S. Cl. .................................. 564/398; 564/214; 564/394
[58] Field of Search ................ 564/398, 214, 211, 394

[56] References Cited

U.S. PATENT DOCUMENTS

| | | | |
|---|---|---|---|
| 3,929,855 | 12/1975 | Summers | 524/254 |
| 3,937,730 | 2/1976 | Vogel et al. | 564/214 |
| 4,200,451 | 4/1980 | Vogel et al. | 71/118 |
| 4,463,191 | 7/1984 | D'Sidocky et al. | 524/254 |

FOREIGN PATENT DOCUMENTS 270548  6/1991  Czechoslovakia.

OTHER PUBLICATIONS

CA 116:128349(b) Beska (Jun. 1991).
Practical Catalytic Hydrogenation pp. 346–349, M. Freifelder (1971).

Primary Examiner—Peter O'Sullivan
Assistant Examiner—B. Burn
Attorney, Agent, or Firm—Marla J. Mathias

[57] ABSTRACT

A process for the preparation of 2-alkyl-6-methyl-N(1'-methoxy-2'-propyl)-aniline by catalytic reductive alkylation wherein at least one mole equivalent of methoxyacetone is reacted with one mole equivalent of 2-alkyl-6-methyl-aniline in a liquid medium without an additional solvent, in the presence of a platinized carbon catalyst and hydrogen and in the presence of an acid cocatalyst under a hydrogen pressure of between $2 \times 10^5$ and $1 \times 10^6$ Pa at a temperature between 20° and 80° C., characterized in that the reaction mixture contains water from the beginning of the reaction and after the hydrogenation, base is added, the reaction mixture is filtered to separate the catalyst and the title compound recovered from the filtrate. The process is particularly useful for the preparation of N-substituted chloracetanilide herbicides.

28 Claims, No Drawings

PROCESS FOR THE PREPARATION OF 2-ALKYL-6-METHYL-N-(1'-METHOXY-2'-PROPYL)-ANILINE AND A PROCESS FOR THE PREPARATION OF THEIR CHLORACETANILIDES

This is a continuation-in-part of Ser No. 07/998,030, filed Dec. 12, 1992, now abandoned.

The present invention relates to an improved process for the preparation of 2-alkyl-6-methyl-N-(1'methoxy-2'-propyl)-aniline and a process for the preparation of 2-alkyl-6-methyl-N-(1'methoxy-2'-propyl)-N-chloracetanilide.

N-alkylaniline derivatives can be used industrially as intermediates in the manufacture of agricultural active substances, particularly herbicides, as described, for example in U.S. Pat. No. 3,937,730. Preparative routes are described briefly in U.S. Pat. No. 3,937,730 but the reductive alkylation method is neither exemplified nor described in detail.

Czechoslovakian patent CS 270 548 describes a process for the preparation of 2-ethyl-6-methyl-N-(1-methoxy-2-propyl)-aniline by reductive alkylation of 2-ethyl-6-methylaniline in the presence of a platinum hydrogenation catalyst and an inorganic acid as protonation catalyst. Drawbacks of this process are that the reaction does not run to completion without further addition of fresh catalyst, and significant catalytic activity is lost on recycling the catalyst. It is difficult to filter the catalyst which is finely divided because the filter becomes clogged. This leads to lengthy filtration times. A further disadvantage from an ecological point of view is the use of excess methoxyisopropanol as solvent.

An improved process for the preparation of 2-alkyl-6-methyl-N-(1'methoxy-2'-propyl)-aniline has been sought which is applicable on an industrial scale and which brings ecological and economic advantages over known processes. A better method of removing the catalyst and cocatalyst by filtration is required, as is the avoidance of additional activated carbon and solvent.

Surprisingly it has now been found that without any loss in yield and purity, a substantially improved separation of the hydrogenation catalyst, acid cocatalyst and end product is achieved by conducting the known preparative process using additional quantities of water during the reductive alkylation, and adding a base to the reaction mixture prior to separating the final product. It has also been found that the reused catalyst shows only minor losses in activity over many cycles so that no or only minor amounts of fresh catalyst must be added to maintain the full activity. It is the object of the present invention to provide an improved process for the preparation of 2-alkyl-6-methyl-N-(1'methoxy-2'-propyl)-aniline of the formula I

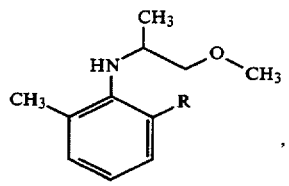

(I)

where R is methyl or ethyl, by catalytic reductive alkylation wherein at least one mole equivalent of methoxyacetone of the formula II

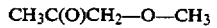

$CH_3C(O)CH_2-O-CH_3$ (II)

is reacted with one mole equivalent of 2-alkyl-6-methylaniline of the formula III

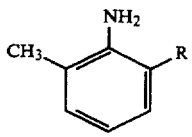

(III)

in a liquid medium without an additional solvent, in the presence of a platinised carbon catalyst and hydrogen and in the presence of an acid cocatalyst under a hydrogen pressure of between $2 \times 10^5$ and $1 \times 10^6$ Pa at a temperature between 20° and 80° C., characterised in that the reaction mixture contains water from the beginning of the reaction and after the hydrogenation, base is added, the reaction mixture is filtered to separate the catalyst and the compound of formula I recovered from the filtrate. R is preferably ethyl.

The starting compounds are available commercially or can be prepared by known methods. Methoxyacetone of formula II can be prepared, for example, by catalytic dehydrogenation of methoxyisopropanol, and the hydrogen recovered for use in the hydrogenation step of the process herein described.

The water content of the reaction mixture may be 5 to 50% by weight, preferably 10 to 40% and more preferably 15 to 30%, related to methoxyacetone. Most preferably the methoxyacetone of formula II is used directly as its azeotrope with water, and contains about 25% by weight of water.

The condensation reaction takes place in an aqueous medium acidified with an acid cocatalyst. The acid cocatalyst used can be for example $H_3PO_4$ or $H_2SO_4$, sulfuric acid being preferred. Small amounts of acid are adequate, for example 0.001 to 0.08 mole equivalents in relation to the amount of 2-alkyl-6-methyl-aniline present.

The reaction between compounds of formula II and III is exothermic and the temperature of the reaction mixture is allowed to rise preferably to between 35° and 60° C., more preferably to between 40° and 50° C. where it is maintained, for example by external cooling if necessary, for hydrogenation.

The catalyst used for hydrogenation is platinum on an activated carbon carrier, sometimes referred to as platinised carbon. The platinum metal is present in an amount of 3 to 6%, preferably 4 to 5% by weight of the carrier. The catalyst has been found to be re-usable over 100 times without detrimental effect on its activity or reaction selectivity. In a preferred embodiment the catalyst is reused, for example in more than 10 to 15 cycles. After this reuse it may be advantageous to add minor amounts of fresh catalyst.

Air should be displaced from the autoclave before the reaction. This may be carried out by flushing the autoclave with an inert gas, e.g. neon, argon, helium or nitrogen. Nitrogen is preferred.

The process can be carried out conveniently in an autoclave equipped with separate gas inlet valves, for example a valve for hydrogen, a valve for nitrogen and optionally an air inlet valve. Hydrogenation is carried out under a hydrogen pressure of preferably 3 to 7 bar, more preferably 4 to 6 bar (1 bar = $1 \times 10^5$ Pascals).

The base added after hydrogenation may be KOH or NaOH, and is preferably NaOH. Sufficient base is added to neutralise the acid cocatalyst which may be recovered from the aqueous phase, e.g. as its salt.

Prior to filtration it is advantageous to displace the unreacted hydrogen in the autoclave with an inert gas, e.g. one of the above-mentioned gases, though nitrogen is preferred. The reaction mixture is allowed to run out of the autoclave through a filter. A pressure difference may be advantageous, e.g. reduced pressure below the filter or pressure may be applied above the filter, meaning the autoclave side. It is preferable to apply nitrogen pressure within the autoclave to expel the mixture completely as well as to reduce the filtration time. The platinised carbon catalyst may be washed with water and dried under a stream of nitrogen gas, e.g. technical grade nitrogen, or an air/nitrogen mixture before it is reused in the next reaction. The title compound forms the organic phase, and is separated from the aqueous phase by known methods and may be purified or used directly in a subsequent process, e.g. for the preparation of agricultural active substances.

A further object of the invention is a process for the manufacture of compounds of the formula IV

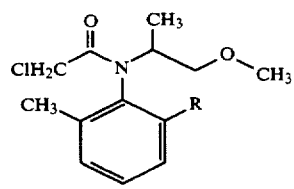

where R is methyl or ethyl, wherein
a) in a first step a catalytic reductive alkylation is performed wherein at least one mole equivalent of methoxyacetone of the formula II

is reacted with one mole equivalent of 2-alkyl-6-methyl-aniline of the formula III

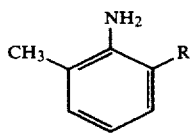

in a liquid medium without an additional solvent, in the presence of a platinised carbon catalyst and hydrogen and in the presence of an acid cocatalyst under a hydrogen pressure of between $2 \times 10^5$ and $1 \times 10^6$ Pa at a temperature between 20° and 80° C., and b) reacting in a second step the compound of formula I with monochloracetic acid chloride and isolating the compound of formula IV, characterised in that, that in the first reaction step a) the reaction mixture contains water from the beginning of the reaction and after the hydrogenation, base is added, the reaction mixture is filtered to separate the catalyst.

Preferences for the first step a) are the same as afore mentioned for preparing compounds of formula I.

Reaction step b) leads to compounds of formula IV, which is described for example in the Canadian patent application No 1 176 659.

Monochloracetic acid chloride may be used equimolar or in an excess amount of up to 20 mol/mol of a compound of formula I. Preferred is an excess of 5 to 15 mol/mol. The reaction can be performed in the presence of an inert solvent such as for example aromatic solvents like benzene, toluene, xylene. It is of particular advantage to use the excess amount of monochloracetic acid chloride as a solvent for the reaction without any further cosolvent.

Reaction temperature may vary between 50° and 130° Celsius. The reaction is advantageously performed in the temperature range of 70° C. to the reflux temperature of the reaction mixture, preferably at the reflux temperature of the reaction mixture.

The washing of the product obtained after the excess monochloracetic acid chloride has been distilled off can be carried out with water at 50° to 100° C. It is advantageous to repeat the washing several times. It is also advantageous to add to the washing water an amount of alkali, particularly sodium hydroxide or potassium hydroxide, to bring the pH value of the water to 4 to 10. The product is subsequently dried by heating at 100° to 120° C. in vacuo.

The reaction step b) can be performed either batchwise or continuously. In carrying out the process continuously it is advantageous to add monochloracetic acid chloride and a compound of formula I simultaneously into the reaction vessel and directly afterwards to concentrate the mixture in vacuo. The hydrogen chloride formed during the reaction is separated in gaseous form and can be compressed and fed into steel cylinders, or dissolved in water to form concentrated hydrochloric acid.

Step a) process according to the invention is furthermore surprising in view of the discussion of reductive alkylation by M. Freifelder on pages 346 to 349 of "Practical Catalytic Hydrogenation" (Wiley Interscience 1971). The removal of reaction water, for example over an anhydrous inorganic salt, is reported to increase yields by shifting the equilibrium towards the condensation product, e.g. an azomethine.

The advantages of step a) process according to the invention are summariser as follows:
  high turnover of the Pt catalyst is achieved without significant loss of activity or selectivity;
  easier isolation of the end products;
  easier separation of the catalyst;
  no organic solvent used in addition to the reactants.

The following examples illustrate the invention in more detail.

EXAMPLE 1

2-ethyl-6-methyl-N-(1'-methoxy-2'-propyl)-aniline 236.1 g (2.01 mol) freshly prepared methoxyacetone (75% methoxyacetone, 25% water) are mixed with 233.9 g (1.73 mol) 2-methyl-6-ethyl-aniline (100%) in an autoclave. 3.7 g Pt—C (5%), previously stored under water, are added to the autoclave with 20 g water. 4.3 g 96% H$_2$SO$_4$ are added carefully dropwise while the mixture is stirred. The autoclave is closed and air flushed out by filling with technical grade N$_2$ to 5 bar, evacuating the autoclave and re-filling with nitrogen three times. The technical grade nitrogen contains between 0.1 and 0.5% by weight oxygen.

The nitrogen is replaced by flushing with hydrogen, evacuation and repeated filling with hydrogen to a pressure of 5 bar. The reaction mixture is stirred and the temperature allowed to rise to between 40° and 45° C. where it is maintained. The H₂ pressure is held using a pressure regulator at between 4.8 and 5.0 bar. The H₂ uptake by the reaction ceases after about 4 hours after which the reaction mixture is cooled to 20° C. The hydrogen is expelled using nitrogen by flushing, evacuation, and refilling with N₂ to a pressure of 5 bar and repeating 3 times. The N₂ pressure is then reduced to atmospheric pressure and the autoclave is opened. 18.75 g NaOH (20%) are added while the reaction mixture is stirred.

The autoclave is closed, nitrogen pumped in again, and the contents pumped through a filter using a nitrogen pressure slightly above atmospheric pressure. The filtercake is the platinised carbon catalyst. 20 g water are added to the autoclave which are run under N₂ through the filtered catalyst to wash it. Moisture remaining in the catalyst is removed by evaporation under a stream of nitrogen for several minutes. The filtered organic phase is isolated from the aqueous phase using a phase separator and yields 354.1 g title compound (98.7% of theory). The catalyst is removed from the filter and returned to the autoclave with a further 20 g water. The autoclave is refilled with nitrogen before repeating the process.

Effect of recycling on catalyst activity

In a series of 20 catalytic hydrogenation reactions, the following results were obtained under the above conditions using a reaction time of 4.5 hours.

2-ethyl-6-methyl-N-(1'-methoxy-2'-propyl)-aniline is abbreviated NAA, and methyl ethyl aniline abbreviated MEA.

|  | Hydrogenation No. | |
| --- | --- | --- |
|  | 1–13 | 14–20 |
| Amount of NAA in organic phase | 97% | 93–96% |
| Turnover (measured on MEA) | 98.5–100% | 96–98%. |

EXAMPLE 2

2-ethyl-6-methyl-N-(1'-methoxy-2'-propyl)-N-chloracetanilide 9.7 g (0.047 Mol) of 2-ethyl-6-methyl-N-(1'-methoxy-2'-propyl)-aniline according to example 1 and 5.05 g (0.05 Mol) triethylamine are mixed with 30 ml water free benzene. 5.65 g (0.05 Mol) chloracetylchlorid in 10 ml benzene is added dropwise under stirring. The mixture is stirred for 2 hours at room temperature, diethylether is added and the mixture is washed several times with water. After separation of the organic phase and the water phase, the organic phase is dried and solvents are removed under vaccum. The product is obtained quantitatively and has a refractive index of $n_D^{20}$: 1.5301.

We claim:

1. A process for the preparation of 2-alkyl-6-methyl-N-(1'methoxy-2'-propyl)-aniline of the formula I

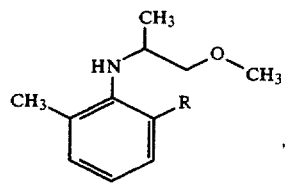

where R is methyl or ethyl, by catalytic reductive alkylation wherein at least one mole equivalent of methoxyacetone of the formula II

is reacted with one mole equivalent of 2-alkyl-6-methyl-aniline of the formula III

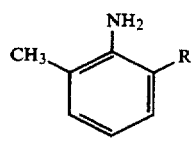

in a liquid medium without an additional solvent, in the presence of a platinised carbon catalyst and hydrogen and in the presence of an acid cocatalyst under a hydrogen pressure of between $2 \times 10^5$ and $1 \times 10^6$ Pa at a temperature between 20° and 80° C., characterised in that the reaction mixture contains 5 to 50% by weight related to methoxyacetone of water at the beginning of the reaction and after the completion of the hydrogenation, base is added, the reaction mixture is filtered to separate the catalyst, which is washed with water and dried under a stream of technical grade nitrogen, and the compound of formula I recovered from the filtrate.

2. A process according to claim 1, wherein R is ethyl.

3. A process according to claim 1, wherein the methoxyacetone of formula II is used directly as its azeotrope with water.

4. A process according to claim 1, wherein the condensation reaction takes place in an aqueous medium acidified with H₃PO₄ or H₂SO₄ as cocatalyst.

5. A process according to claim 4, wherein sulfuric acid is used as acid cocatalyst.

6. A process according to claim 4, wherein 0.001 to 0.08 mole equivalents of acid cocatalyst are used in relation to the amount of 2-alkyl-6-methyl-aniline present.

7. A process according to claim 1, wherein the reaction between compounds of formula II and III is carried out at a temperature of between 35° and 60° C.

8. A process according to claim 1, wherein the hydrogenation catalyst is platinum on an activated carbon carder.

9. A process according to claim 8, wherein the platinum metal is present in an amount of 3 to 6% by weight of the carrier.

10. A process according to claim 1, wherein the base is KOH or NaOH.

11. A process according to claim 1, wherein after hydrogenation, the autoclave is flushed through with nitrogen gas.

12. A process according to claim 1, wherein nitrogen pressure is applied within the autoclave during filtration to remove the catalyst.

13. A process according to claim 1, wherein the recovered catalyst is recycled.

14. A process according to claim 13, wherein the catalyst is recycled up to 100 times.

15. A process for the preparation of compounds of the formula IV

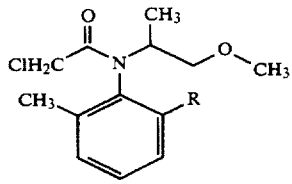

where R is methyl or ethyl, wherein a) in a first step a catalytic reductive alkylation is performed wherein at least one mole equivalent of methoxyacetone of the formula II

is reacted with one mole equivalent of 2-alkyl-6-methyl-aniline of the formula III

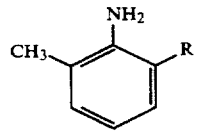

in a liquid medium without an additional solvent, in the presence of a platinised carbon catalyst and hydrogen and in the presence of an acid cocatalyst under a hydrogen pressure of between $2 \times 10^5$ and $1 \times 10^6$ Pa at a temperature between 20° and 80° C., and b) reacting in a second step the compound of formula I with monochloracetic acid chloride and isolating the compound of formula IV, characterised in that, that in the first reaction step a) the reaction mixture contains 5 to 50% by weight related to methoxyacetone of water at the beginning of the reaction and after the completion of the hydrogenation, base is added, the reaction mixture is filtered to separate the catalyst, which is washed with water and dried under a stream of technical grade nitrogen.

16. A process according to claim 15, wherein R is ethyl.

17. A process according to claim 15, wherein the methoxyacetone of formula II is used directly as its azeotrope with water.

18. A process according to claim 15, wherein the condensation reaction takes place in an aqueous medium acidified with $H_3PO_4$ or $H_2SO_4$ as cocatalyst.

19. A process according to claim 18, wherein sulfuric acid is used as acid cocatalyst.

20. A process according to claim 18, wherein 0.001 to 0.08 mole equivalents of acid cocatalyst are used in relation to the amount of 2-alkyl-6-methyl-aniline present.

21. A process according to claim 15, wherein the reaction between compounds of formula II and III is carried out at a temperature of between 35° and 60° C.

22. A process according to claim 15, wherein the hydrogenation catalyst is platinum on an activated carbon carrier.

23. A process according to claim 22, wherein the platinum metal is present in an amount of 3 to 6% by weight of the carrier.

24. A process according to claim 15, wherein the base is KOH or NaOH.

25. A process according to claim 15, wherein after hydrogenation, the autoclave is flushed through with nitrogen gas.

26. A process according to claim 15, wherein nitrogen pressure is applied within the autoclave during filtration to remove the catalyst.

27. A process according to claim 15, wherein the recovered catalyst is recycled.

28. A process according to claim 27, wherein the catalyst is recycled up to 100 times.

* * * * *